US006485455B1

(12) United States Patent
Thompson et al.

(10) Patent No.: US 6,485,455 B1
(45) Date of Patent: *Nov. 26, 2002

(54) CATHETER STEERING ASSEMBLY PROVIDING ASYMMETRIC LEFT AND RIGHT CURVE CONFIGURATIONS (75) Inventors: Russell B. Thompson, Menlo Park, CA (US); Robert A. Kelley, Newark, CA (US); Fernando Pumares, San Bruno, CA (US)

(73) Assignee: EP Technologies, Inc., Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/273,044

(22) Filed: Mar. 19, 1999

Related U.S. Application Data (60) Continuation of application No. 08/812,195, filed on Mar. 6, 1997, now Pat. No. 5,891,088, which is a continuation of application No. 08/632,762, filed on Apr. 16, 1996, now abandoned, which is a continuation of application No. 08/324,585, filed on Oct. 18, 1994, now abandoned, which is a continuation of application No. 08/058,319, filed on May 6, 1993, now Pat. No. 5,358,478, which is a continuation-in-part of application No. 07/790,207, filed on Nov. 8, 1991, now Pat. No. 5,273,535, and a continuation-in-part of application No. 07/991,474, filed on Dec. 16, 1992, now Pat. No. 5,254,088, which is a continuation of application No. 07/736,384, filed on Jul. 26, 1991, now abandoned, which is a division of application No. 07/473,667, filed on Feb. 2, 1990, now abandoned.

(51) Int. Cl.[7] ............................................. A61M 31/00
(52) U.S. Cl. .................................... 604/95.04; 604/528
(58) Field of Search ........................... 604/95, 282, 159, 604/170, 528; 600/585, 433–5, 108, 114

(56) References Cited

U.S. PATENT DOCUMENTS

| 3,892,228 A | | 7/1975 | Mitsui |
| 3,897,775 A | | 8/1975 | Furihata |
| 4,543,090 A | | 9/1985 | McCoy |
| 4,723,936 A | | 2/1988 | Buchbinder et al. |
| 4,758,222 A | | 7/1988 | McCoy |
| 4,826,087 A | | 5/1989 | Chinery |
| 4,934,340 A | | 6/1990 | Ebling et al. |
| 4,941,454 A | | 7/1990 | Wood et al. |
| 4,942,866 A | | 7/1990 | Usami |
| 4,944,727 A | | 7/1990 | McCoy |
| 4,947,827 A | * | 8/1990 | Opie et al. .................. 600/108 |
| 4,984,581 A | | 1/1991 | Stice |
| 5,055,101 A | | 10/1991 | McCoy |

(List continued on next page.)

OTHER PUBLICATIONS

"Preliminary Report on a New Method of Intestinal Intubation with the Aid of a Flexible Stylet with Controllable Tip", Smith et al., Surgery, vol. 27, No. 6, pp. 817–821.*

"Preliminary Report on a New Method of Intestinal Intubation with the Aid of a Flexible Stylet with Controllable Tip", Grafton A. Smith, M.D.; 1949; pp. 817–821; Minneapolis, MN.

Primary Examiner—Anhtuan T. Nguyen
Assistant Examiner—Michael M. Thompson
(74) Attorney, Agent, or Firm—Bingham McCutchen LLP (57) ABSTRACT A catheter has an electrode tip assembly that is bendable at the selection of the user in two different directions. The electrode tip assembly assumes different asymmetric predetermined curve configurations when bent in the two directions and is manipulated by means of steering wires adjustably connected tangentially to the lateral edges of a rotatable cam located in the catheter handle.

14 Claims, 4 Drawing Sheets

U.S. PATENT DOCUMENTS

| | | |
|---|---|---|
| 5,090,956 A | 2/1992 | McCoy |
| 5,108,368 A | 4/1992 | Hammerslag et al. |
| 5,114,402 A | 5/1992 | McCoy |
| 5,123,421 A | 6/1992 | Sinofsky |
| 5,254,088 A * | 10/1993 | Lundquist et al. .......... 600/585 |
| 5,273,535 A * | 12/1993 | Edwards et al. ......... 604/95.01 |
| 5,358,478 A * | 10/1994 | Thompson et al. ...... 604/95.04 |
| 5,358,479 A * | 10/1994 | Wilson .................... 604/95.01 |
| 5,482,037 A * | 1/1996 | Borghi ....................... 600/381 |
| 5,820,591 A * | 10/1998 | Thompson et al. ...... 604/95.01 |
| 5,891,088 A * | 4/1999 | Thompson et al. ...... 604/95.04 |

\* cited by examiner

CATHETER STEERING ASSEMBLY PROVIDING ASYMMETRIC LEFT AND RIGHT CURVE CONFIGURATIONS

RELATED APPLICATION DATA

This application is a continuation of application Ser. No. 08/812,195, filed Mar. 6, 1997, now U.S. Pat. No. 5,891,088, which is a continuation of application Ser. No. 08/632,762, filed Apr. 16, 1996, now abandoned, which is a continuation of application Ser. No. 08/324,585, filed Oct. 18, 1994, now abandoned, which is a continuation of application Ser. No. 08/058,319, filed May 6, 1993, now U.S. Pat. No. 5,358,478, which is a continuation-in-part of application Ser. No. 07/790,207, filed Nov. 8, 1991, now U.S. Pat. No. 5,273,535, and a continuation-in-part of application Ser. No. 07/991,474, filed Dec. 16, 1992, now U.S. Pat. No. 5,254,088, which is a continuation of application Ser. No. 07/736,384, filed Jul. 26, 1991, now abandoned, which, is a divisional application of application Ser. No. 07/473,667, filed Feb. 2, 1990, now abandoned.

FIELD OF THE INVENTION

The invention generally relates to steering controls for catheters. In a more specific sense, the invention relates to catheters that can be steered and manipulated within interior regions of the body from a location outside the body.

BACKGROUND OF THE INVENTION

Physicians make widespread use of catheters today in medical procedures to gain access into interior regions of the body. It is important that the physician can control carefully and precisely the movement of the catheter within the body, especially during procedures that ablate tissue within the heart. These procedures, called electrophysiological therapy, are becoming more widespread for treat cardiac rhythm disturbances.

During these procedures, a physician steers a catheter through a main vein or artery (which is typically the femoral artery) into the interior region of the heart that is to be treated. The physician then further manipulates a steering mechanism to place the electrode carried on the tip of the catheter into direct contact with the tissue that is to be ablated. The physician directs radio frequency energy into the electrode tip to ablate the tissue and form a lesion.

Cardiac ablation especially requires the ability to precisely bend and shape the tip end of the catheter to position the ablation electrode.

SUMMARY OF THE INVENTION

The invention provides a catheter having a distal tip section that is bendable at the selection of the user in two different directions. The distal tip section assumes different predetermined curves when bent in each direction. The degree of bending or shape of the predetermined curve can be adjusted in accordance with the invention.

The invention provides a catheter having a body that is bendable in different first and second directions in response, to external forces. The catheter includes a steering mechanism that is movable in two paths for applying different external bending forces on the body and wherein the forces can be adjusted by providing for a different length of travel paths for causing bending forces in the first and second directions.

The steering mechanism includes a first actuator that operates in response to movement of the steering mechanism in the first path. The first actuator bends the body in the first direction into a first adjustable predetermined nonlinear shape.

The steering mechanism also includes a second actuator that operates in response to movement of the steering mechanism in the second path. The second actuator bends the body in the second direction into a second adjustable predetermined nonlinear shape. The second shape is different from the first shape.

In one embodiment, the bendable body includes a flexible wire member having left and right faces. In this arrangement, the steering mechanism includes left and right steering wires. The distal ends of the steering wires are attached, respectively, to the left and right faces of the wire member.

In this embodiment, the first actuator places the left steering wire into tension to bend the wire member to the left into the first adjustable nonlinear shape. The second actuator places the right steering wire into tension to bend the wire member to the right into the second adjustable nonlinear shape. The steering wires cause asymmetric bending of the wire member by virtue of the fact that the first and second actuators cause the left and right steering wires to travel different distances.

In one embodiment, the points of attachment of the distal ends of the left and right steering wires are generally symmetrically spaced on the left and right faces of the wire member. In another arrangement, the points of attachment of the distal ends of the left and right steering wires are generally asymmetrically spaced on the left and right faces of the wire member.

In one embodiment, the steering mechanism includes a rotatable cam to the lateral edges of which the proximal ends of the left and right steering wires are adjustably attached. A lever mechanism rotates the rotatable cam to the left and to the right.

In this arrangement, the first actuator includes a first cam surface formed on the left side of the rotatable cam. The first cam surface bears against and tensions the left steering wire in response to rotation of the rotatable cam to the left.

Also in this arrangement, the second actuator includes a second cam surface formed on the right side of the rotatable cam. The second cam surface is configured differently from the first cam surface and bears against and tensions the right steering wire in response to rotation of the rotatable cam to the right.

In one embodiment, the first and second cam faces form curves having different radii. Alternatively, the cam faces may be symmetrical but asymmetric steering is accomplished by adjusting the amount of travel of the steering wires.

The steering wires are preferably attached tangentially to the lateral edges of the rotatable cam and can be adjusted so that rotation of the rotatable cam results in a multitude of selectable different left and right curve shapes. In accordance with the preferred embodiment of the invention the control wires extend through adjustable stop members threaded into threaded openings in the lateral edges of the rotatable cam. The proximal ends of the wires are fixed to terminal blocks that are engaged by the stops upon rotation of the rotatable cam to thereby selectively apply tension to the wires. Preferably the steering wires are attached to the terminal blocks by having the ends thereof being bent at an angle exceeding 90°, in fishhook fashion, and being soldered into the blocks.

DESCRIPTION OF THE PREFERRED EMBODIMENTS

Figure 1:
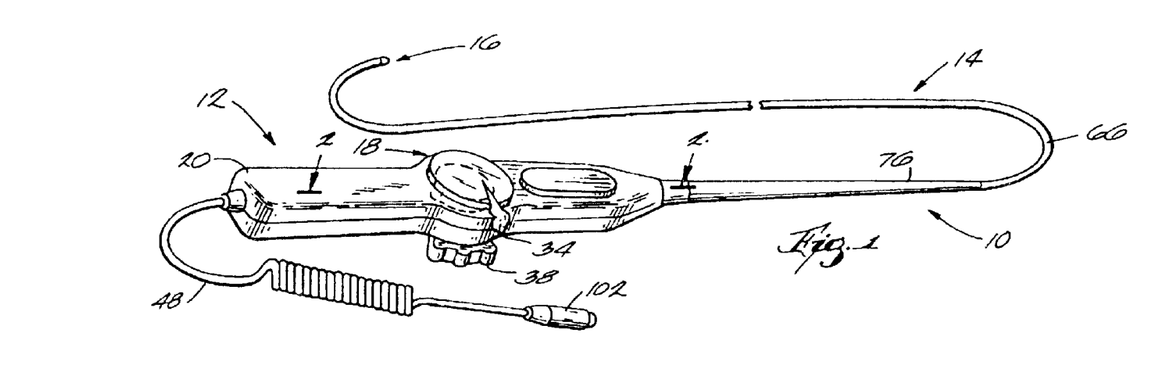
FIG. 1 is a perspective view of a catheter that embodies the features of the invention.

FIG. 1 shows a steerable catheter 10 that embodies the features of the invention. As there shown, the catheter 10 includes three main parts or assemblies: the handle assembly 12, the guide tube assembly 14, and the electrode tip assembly 16. An electrical cable 48 for providing power to an electrode at the distal tip of the catheter attaches to the back of the housing 20.

The catheter 10 can be used in many different environments. This specification will describe the catheter 10 as used to provide electrophysiologic therapy in the interior regions of the heart.

When used for this purpose, a physician grips the handle assembly 12 to steer the guide tube assembly 14 through a main vein or artery (which is typically the femoral arterial) into the interior region of the heart that is to be treated. The physician then further manipulates a steering mechanism 18 on the handle assembly 12 (which will be described later) to place the electrode tip assembly 16 in contact with the tissue that is to be ablated. The physician directs radio frequency energy into the electrode tip assembly 16 to ablate the tissue contacting the electrode tip assembly 16.

Figure 2:
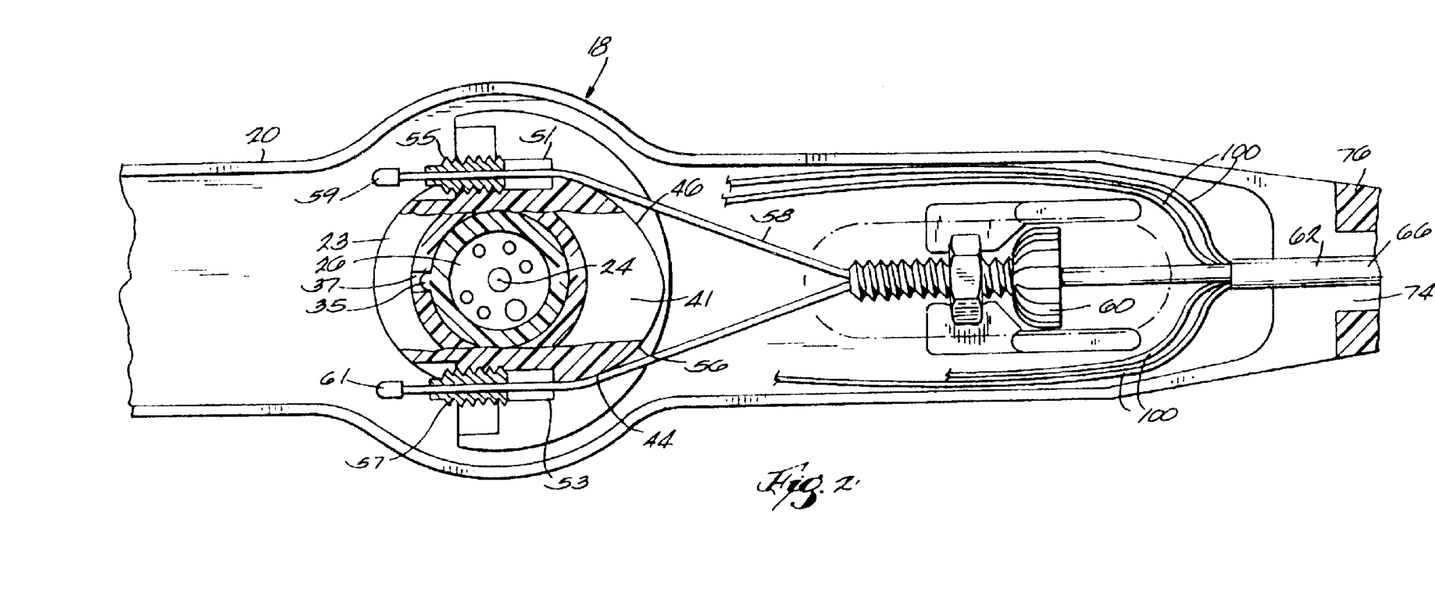
FIG. 2 is a top central sectional view of the handle portion of the catheter of FIG. 1 taken generally along Line 2—2 with parts broken away for clarity.

As FIG. 2 best shows the handle assembly 12 includes a housing 20 that encloses the steering mechanism 18. The steering mechanism 18 includes a rotatable cam 23 carried on a screw 24 within the housing 20. The rotatable cam 23 is seated for rotation between top washer 26 which bears on a shoulder 27 and a bottom washer. Screw 24 is threaded into a central opening in washer 26. An external steering lever 34 is adhesively bonded or ultrasonically welded to the top of the rotatable cam 23. A tab 35 on the steering lever 34 is seated in a notch 37 in rotatable cam 23. The steering lever 34 also seats against an O-ring (not shown). Further details regarded the O-rings and similar assembly details are described in the above-mentioned copending application Ser. No. 790,207, the entire disclosure of which is herein incorporated by reference.

Movement of the steering lever 34 by the user rotates the rotatable cam 23 about the screw 24 within the housing 20. Clockwise movement of the steering level rotates the rotatable cam 23 to the right. Counterclockwise movement of the steering wheel rotates the rotatable cam 23 to the left. Contact between the steering lever 34 and the side of the housing 20 physically limits the range of left and right rotation of the rotatable cam 23 within the housing 20.

The steering mechanism 18 also includes an external locking lever 38 has hexagonal opening into which the hexagonal head of the screw 24 is seated and bonded by an adhesive. The locking lever 38 seats against another O-ring. Movement of the locking lever 38 rotates the screw 24 in the threaded opening in washer 26. Clockwise rotation of the locking lever 38 tightens the screw 24 to increase the seating force on the rotatable cam 23. When moved fully clockwise into contact against the housing 20, the locking lever 38 imposes a seating force that restricts rotation of the rotatable cam 23 by the steering lever 34. Counterclockwise movement of the locking lever 34 loosens the screw 24 to decrease the seating force and free the rotatable cam 23 for rotation.

Figure 9:
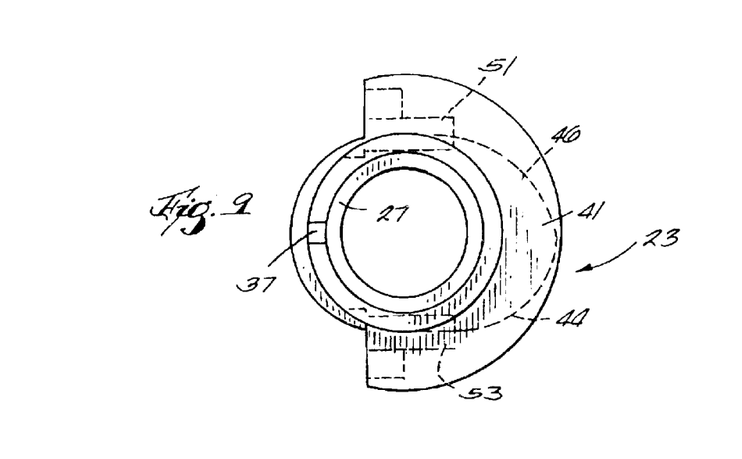
FIG. 9 is a top view of a rotatable cam used in the steering mechanism.
Figure 10:
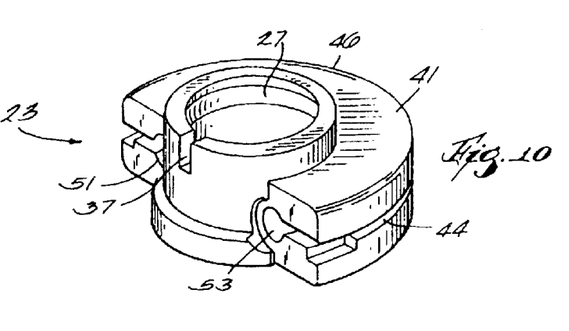
FIG. 10 is a perspective view of the cam shown in FIG. 9.

The rotatable cam 23 includes an asymmetrically shaped forward cam face 41. The forward cam face 41 is oriented toward the front of the housing 20, where the guide tube assembly 14 attaches. The forward cam face includes a right side cam surface 44 and a left side cam surface 46. Surfaces 44 and 46 are located at the bottoms of grooves in the lateral edges of rotatable cam 23. Surfaces 44 and 46 may either be of the same (symmetric) radii or may be asymmetrically shaped. In the former instance asymmetric steering of the catheter distal tip is accomplished by adjusting the distance traveled by the steering wires and, as a result, the amount of tension applied thereto.

Figure 8:
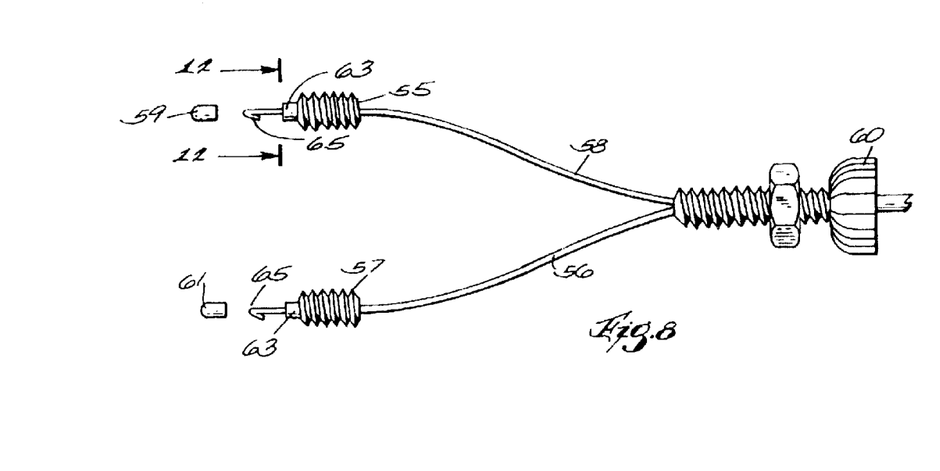
FIG. 8 shows the steering mechanism of the catheter with parts disassembled for clarity.
Figure 11:
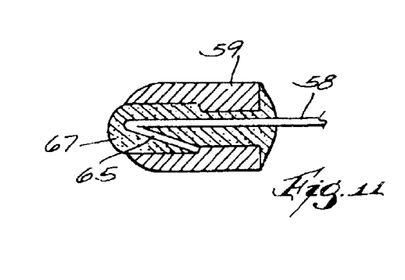
FIG. 11 is a cross sectional view of the steering wire terminal of the steering mechanism; and, FIG. 12 is a cross sectional view taken along Line 12—12 of FIG. 8 showing the adjustable stop used in the steering mechanism.
Figure 12:
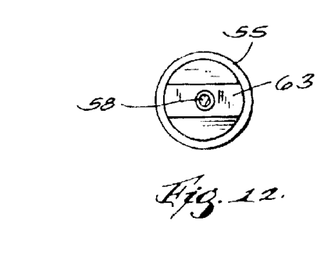

The rotatable cam 23 is provided on its lateral edges with threaded holes 51 and 53 into which adjustable stops 55 and 57, respectively, are threaded. The proximal ends of right and left catheter steering wires 56 and 58, pass through central openings in stops 55 and 57 and are attached to steering wire terminals 59 and 61. Steering wires 56 and 58 are bent in fishhook fashion (at an angle greater than 90° at their proximal ends 65 and are soldered (67) to the interior of the terminal blocks 59 and 61 (as best seen in FIGS. 8 and 11) in order to firmly anchor the wire ends within the terminal blocks. In order to facilitate adjustment of stops 55 and 57, they are provided with a flattened proximal end 63 which can be engaged by a wrench or similar tool in order to rotate the stops and thus adjust the distance that the stops extend proximally from the edges of rotatable cam 23.

The steering wires 56 and 58 extend from the stops 55 and 57 along the associated left and right side surfaces 44 and 46 of the cam face 41. The steering wires exit the front of the housing 20 through the interior bore of a tension screw assembly 60.

As will be described in greater detail later, the distal ends of the steering wires 56 and 58 are attached to the electrode tip assembly 16. They extend from the tension screw assembly 60 through the guide tube assembly 14 to the electrode tip assembly 16.

As also will be described in greater detail, the adjustable wire stops 55, 57 in association with the terminal blocks 59, 61 and cam faces 44 and 46 translate rotation of the rotatable cam 23 into lateral pulling movement of the steering wires 56 and 58 attached to the electrode tip assembly 16.

Figures 5, 6, 7:
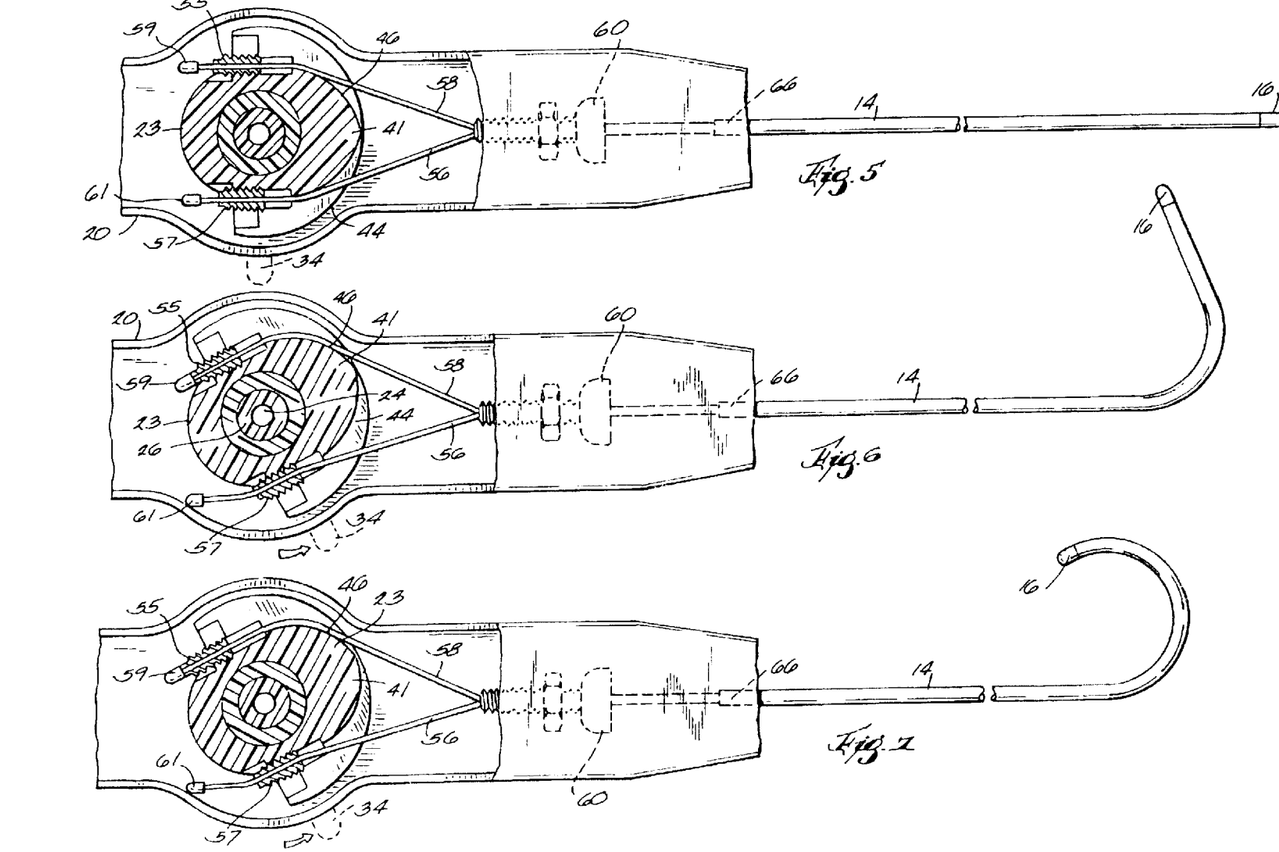
FIG. 5 is a top view of the catheter in the unbent position with parts broken away to show the steering mechanism.
FIG. 6 is top view of the catheter of FIG. 5 steered to the left.
FIG. 7 is a top view of the catheter of FIG. 5 with the steering mechanism adjusted to a different setting and steered to the left at a different curvature.

By rotating the rotatable cam 23 to the left as shown in FIG. 6 (by moving the steering lever 34 counterclockwise), the left steering wire stop 55 bears against the left terminal block 59 and cam surface 46. This movement tensions the left steering wire 58 to impose a discrete, constant pulling force that causes the electrode tip assembly 16 to bend to the left in a desired curvature. If a different degree of curvature is desired, for example, as shown in FIG. 7, stop 55 is rotated to extend it distally, thus adjusting the curvature as shown. Also, since cam surface 44 and 46 are asymmetric in shape, the range of possible curvatures is different for the right and left wires. Thus a nearly infinite variety of asymmetric curve shapes is possible by adjustment of the stops. In practice, catheters having a standard number of preset asymmetric curvatures can be factory produced, all using exactly the same component parts.

By rotating the rotatable cam 23 to the right (by moving the steering lever 34 clockwise), tension is applied to the right steering wire 56 in exactly the same manner as described in connection with wire 58, causing the electrode tip assembly 16 to bend to the right.

Rotation of the tension screw assembly 60 additionally varies the amount of slack (i.e., tension) in the steering wires 56 and 58. This controls the responsiveness of the electrode tip assembly 16 to rotation of the rotatable cam 23.

The component parts of the handle assembly 12 can be constructed of various materials, depending upon the durability needed and the sterilization process used. For example, when ETO sterilization is used, the housing 20 and bottom washer 28 can be made of a polycarbonate material. In this arrangement, the rotatable cam 23, steering lever 34, and locking lever 38 can be made of a Delrin material. These plastic materials are durable and EtO sterilizable. In this assembly, the nuts, pins, and screw 24 are preferably made of a corrosion resistant metallic material such as brass or stainless steel.

Figures 3, 4:
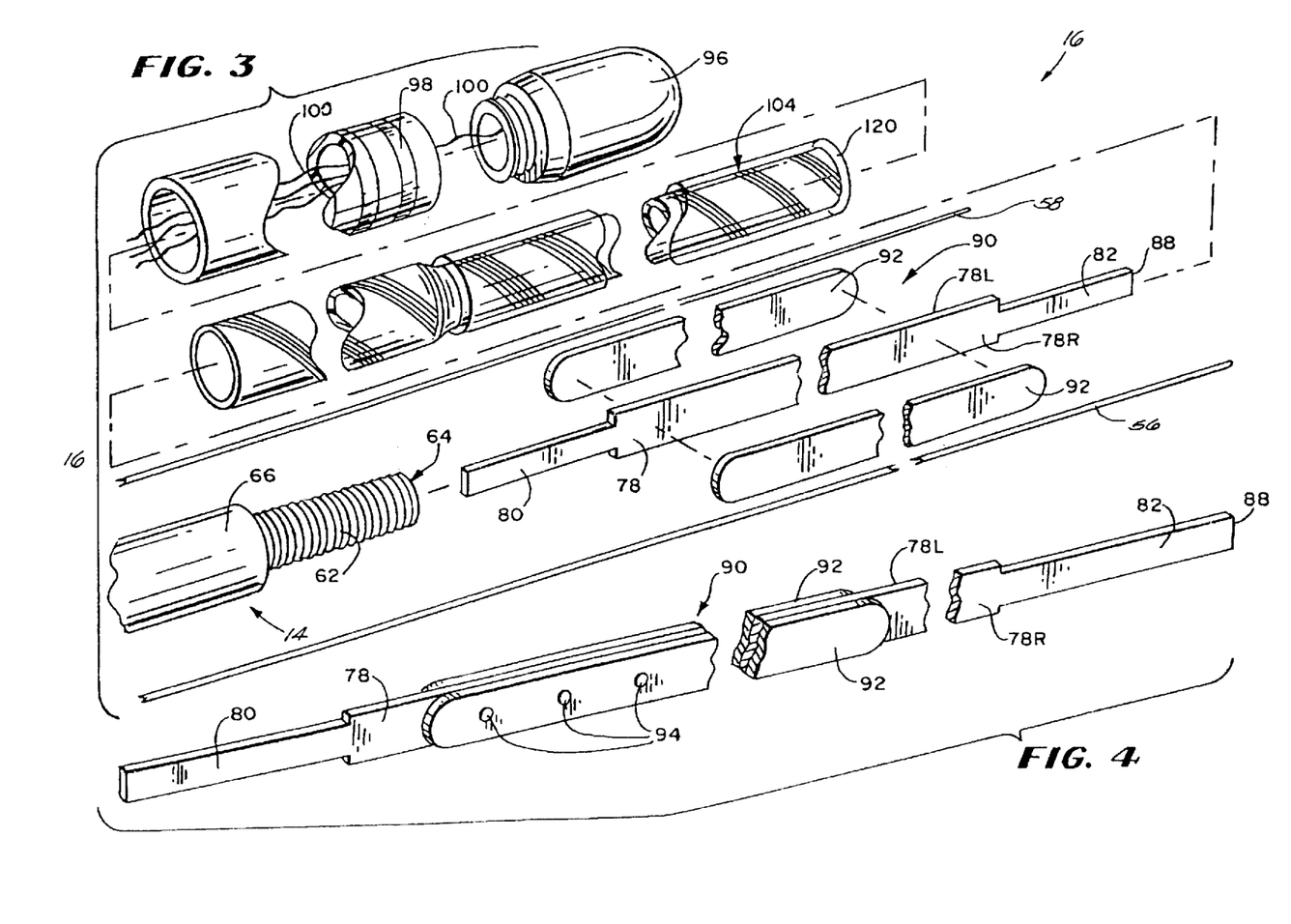
FIG. 3 is an exploded view of the electrode tip assembly of the catheter.
FIG. 4 is a perspective view of the stiffening assembly for the support wire of the catheter.

As FIG. 3 shows, the guide tube assembly 14 includes a flexible shaft 62 attached to the handle assembly 12. The flexible shaft 62 encloses an interior bore 64. The steering wires 56 and 58 pass through the interior bore 64.

The shaft 62 may constructed in various ways. In the embodiment shown in FIG. 3, the shaft 62 comprises a length of stainless steel coiled into a flexible spring enclosing the interior bore 64. A sheath 66 of extruded plastic material containing wire braids encloses the coil. The sheath 66 is preferably made from a thermoplastic material, such as a polyurethane, a polyolefin or polyetherpolyamide block copolymer.

Alternatively the shaft 62 comprises a slotted, stainless steel tube enclosing the interior bore. Further details of such slotted shafts are disclosed in pending Lundquist U.S. patent application Ser. No. 07/657,106 filed Feb. 15, 1991 and entitled "Torquable Catheter 10 and Method."

The handle assembly 12 includes a tubular stem 74 though which the proximal end of the guide tube assembly 14 extends for attachment to the tension screw assembly 60. Adhesive attaches the proximal end of braided sheath 66 to stem 74. The guide tube assembly 14 can be made in various lengths. In the case of cardiac ablation catheters, the guide tube assembly 14 is usually about 100 cm in length.

As FIGS. 1 and 2 show, a sleeve 76 couples the guide tube assembly 14 to the handle assembly 12. Adhesive secures one end of the sleeve 76 to the handle stem 74. The sleeve 76 includes an interior bore that progressively tapers from the handle stem 74 into a tight interference fit about the sheath 66 of the guide tube assembly 14. The exterior of the sleeve 76 also tapers, extending about 4 to 5 inches beyond the front of the handle housing 20.

The sleeve 76 is made of a material having a high coefficient of friction, like Krayton G2703. The sleeve 76 provides a gripping surface to help the user manipulate the catheter 10. When used in association with the slotted tube, the sleeve 76 also significant enhances the transmission of torque from the handle assembly 12 to the electrode tip assembly 16 through the guide tube assembly 14.

The electrode tip assembly 16 includes a bendable main support wire or spring 78 having left and right faces 78L and 78R. In the illustrated embodiment, the main support wire, 78 is made of stainless steel flat wire stock in an elongated shape about 0.035 inch wide and about 0.005 inch thick. The main support wire 78 is about 3 inches in total length.

The opposite ends of the main support wire 78 are cut away to form stepped shoulders 80 and 82. In the illustrated embodiment, the shoulders 80 and 82 are about 0.024 inch wide and aligned along the centerline of the main support wire 78. Each shoulder 80 and 82 is about 0.12 inch in length.

As FIG. 3 shows, one stepped shoulder 80 fits within the distal end of the flexible guide tube shaft 62 to append the electrode tip assembly 16 to the guide tube assembly 14. When properly oriented, the left and right faces 78L and 78R of the main support wire 78 lie in a plane that is generally parallel to the axis about which the rotatable cam 23 rotates. Stated differently, when the user holds the handle assembly 12 in a horizontal plane, the left and right faces 78L and 78R of the main support wire 78 lie in a vertical plane.

As FIG. 3 shows, the distal end of the left steering wire 58 is soldered to the left face 78L of the main support wire 78. When pulled by left rotation of the rotatable cam 23, the left steering wire 58 bends the main support wire 78 to the left.

Also, the distal end of the right steering wire 56 is soldered to the right face 78R of the main support wire 78. When pulled by right rotation of the rotatable cam 23, the right steering wire 56 bends the main support wire 78 to the right.

In the illustrated embodiment, the stiffness of the main support wire 78 is not uniform, but varies along its length. Its stiffest point is near its proximal end region, where it joins the guide tube shaft 62. Its stiffness is least at the tip end 88 of the shoulder 82. By varying the stiffness of the main support wire 78 between its proximal end and its distal tip end 88, the base of the electrode tip assembly 16 (where it joins the guide tube assembly 14) resists bending and buckling. The bending forces generated by the steering wires 56 and 58 are directed toward the distal tip end 88 of the main support wire 78. The variable stiffness of the main support wire 78 concentrates the bending forces at the distal tip end 88 of the electrode tip assembly 16.

There are various ways to varying the stiffness of the main support wire 78 along its length. One way (not shown) is to vary the thickness of the main support wire 78 as it is manufactured, so that it is thickest (i.e., most stiff) near the shoulder 80 that, in use, is fitted within the guide tube shaft 62.

In the illustrated and preferred embodiment (see FIG. 4), a stiffening spring assembly 90 stiffens the center support near the distal end of the guide tube shaft 62. The stiffening spring assembly 90 includes two leaf springs 92 that sandwich the main support wire 78 between them. Each leaf spring 92 is made of stainless steel flat wire stock in an elongated shape that is about 0.035 inch wide and about 0.0025 inch thick.

The stiffening spring assembly 90 can be sized and configured to provide the degrees of stiffness and variance wanted. In the illustrated embodiment, the stiffening spring assembly 90 stiffens the main support wire 78 beginning about 0.030 to 0.050 inch from the inner edge of the attachment shoulder 80 and extending from there about 1.5 inches.

In the illustrated embodiment, spot welds 94 secure the leaf springs 92 to the main support wire 78. The three spot welds 94 shown are clustered near the proximal end of the stiffening spring assembly 90. There, they are evenly spaced, with the most distal spot weld 94 being about 0.10 inch from the proximal end of the stiffening spring assembly 90.

In the illustrated embodiment, the distal end of the electrode tip assembly 16 carries an ablation tip electrode 96 and three ring electrodes 98. Interior conducting wires 100 are connected to the tip electrode 96 and, the three ring electrodes 98. The conducting wires 100 extend along the main support wire 78, through the interior bore of the guide tube shaft 62, and into the handle housing 20 to join the cable 48 that extends from the rear of the housing 20.

The cable 48 ends with plugs 102. The plugs 102 connect with appropriate conventional catheter control equipment (not shown). The conducting wires 100 transfer electrical current from the ring electrodes 98 indicative of electrical activity within the heart. The conducting wires 100 also transfer radio frequency energy to the tip electrode 96 to carry out ablation procedures within the heart.

There are various ways of securing the attachment between the electrode tip assembly 16 and the guide tube assembly 14. The illustrated embodiment employs a reinforcing sleeve assembly 104 for this purpose. The reinforcing sleeve assembly 104 holds the steering wires 56 and 58 in close intimate contact against the main support wire 78. Isolation of the conducting wires 100 from the steering wires 56 and 58 prevents kinking and chafing of the conducting wires 100 during bending operations.

The materials used to make the reinforcing sleeve assembly 104 can vary. shrink tubes 114 can be made from medical grade TFE Teflon material having a 2 to 1 shrink ratio. A reinforcing fabric 116 is wrapped in tension over first tube 114 as a single spiral about the tube 114 to obtain a desired, closely spaced pitch. In the illustrated embodiment the fabric 116 is wrapped to a pitch of about 18 to 20 wraps per inch. The preferred material has a wall thickness (after heat shrinkage) of about 0.003 to 0.0045 inch. In the illustrated embodiment, the fabric 116 is a Kevlar 49 Yarn (which is available from DuPont) . This material has a tensile strength of about 410,000 lbs/in$^2$ and a modulus of about 18,000,000 lbs/in$^2$.

An outer tube 120 covers the reinforcing sleeve assembly 104. The tip electrode 96 is soldered to the center support 78 and ring electrodes 98 are attached to the conducting wires 100 and joined to the outer tube 120 by conventional methods to complete the electrode tip assembly 16.

In the illustrated embodiment, the curvature assumed upon bending the electrode tip assembly 16 to the left is different than the curvature assumed upon bending the electrode tip assembly 16 to the right. The electrode tip assembly 16 assumes one curvature when bent to the left and a different curvature when bent to the right. These different left and right curvatures provide the physician with flexibility in steering the tip electrode 96 into position. These differing curvatures as referred to herein as asymmetric curves.

In addition to the use of a rotatable cam to cause different amounts of travel of the left and right steering wires, it is contemplated that such different amounts of travel can also be caused by means of other mechanisms, as well. For example, a rotatable gear can be intermeshed with a pair of movable toothed racks to form a rack and pinion arrangement. In such case the two racks can be configured differently, or provided with stops to limit the travel in one direction more than in other.

Various features of the invention are set forth in the following claims.

What is claimed is:

1. A steering assembly for applying bending forces to a flexible body, comprising:

a handle;

a moveable component moveably connected to said handle;

first and second steering wires each having a proximal end attached to said moveable component and a distal end attached to the flexible body, wherein movement of said moveable component in a first direction applies tension to said first steering wire causing the flexible body to bend in a first multitude of selected curved shapes, and movement of said moveable component in a second direction applies tension to said second steering wire causing said flexible body to bend in a second multitude of selected curved shapes, said first multitude of curved shapes being different from said second multitude of curve shapes.

2. The steering assembly of claim 1, comprising a guide tube having a distal end attached to the flexible body and a proximal end attached to said handle.

3. The steering assembly of claim 2, wherein said guide tube comprises a length of wire coiled into a flexible spring, said coiled flexible spring defining an internal bore which encloses said first and said second steering wires.

4. The steering assembly of claim 1, wherein the flexible body comprises a flexible wire member having a left face and a right face, said left face being attached to the distal end of a first one of said first and second steering wires, said right face being attached to the distal end of second one of said first and second steering wires.

5. The steering assembly of claim 1, wherein the respective proximal ends of said first and second steering wires are attached to said moveable component by respective adjustable connections.

6. The steering assembly of claim 1, wherein said moveable component comprises a rotatable cam, a first face of said cam having a different radius of curve that a second face of said cam.

7. The steering assembly of claim 6, wherein said proximal end of said first steering wire is tangentially attached to a lateral edge of said first face of said cam; and, said proximal end of said second steering wire is tangentially attached to a lateral edge of said second face of said cam.

8. A steering assembly for applying bending forces to a flexible body, comprising:

a handle;

a moveable component moveably coupled to said handle;

first and second steering wires each having a proximal end attached to said moveable component and a distal end attachable to the flexible body, wherein the steering assembly is adapted to cause an attached flexible body to bend in a first multitude of selected curved shapes in response to tension in said first steering wire caused by movement of said moveable component in a first direction, and is further adapted to cause an attached flexible body to bend in a second multitude of selected curved shapes in response to tension in said second steering wire caused by movement of said moveable component in a second direction, said first multitude of curved shapes being different from said second multitude of curve shapes.

9. The steering assembly of claim 8, further comprising a guide tube having a distal end attachable to the flexible body and a proximal end attached to said handle.

10. The steering assembly of claim 9, wherein said guide tube comprises a length of wire coiled into a flexible spring, said coiled flexible spring defining an internal bore which encloses said first and said second steering wires.

11. The steering assembly of claim 8, wherein the flexible body comprises a flexible wire member having a left face and a right face, said left face being attached to the distal end of a first one of said first and second steering wires, said right face being attached to the distal end of a second one of said first and second steering wires.

12. The steering assembly of claim 8, wherein the respective proximal ends of said first and second steering wires are attached to said moveable component by respective adjustable connections.

13. The steering assembly of claim 8, wherein said moveable component comprises a rotatable cam, a first face of said cam having a different radius of curvature than a second face of said rotatable cam.

14. The steering assembly of claim 13, wherein said proximal end of said first steering wire is tangentially attached to a lateral edge of said first face of said cam, and said proximal end of said second steering wire is tangentially attached to a lateral edge of said second face of said cam.

* * * * *

UNITED STATES PATENT AND TRADEMARK OFFICE
CERTIFICATE OF CORRECTION

PATENT NO. : 6,485,455 B1 Page 1 of 1
DATED : November 26, 2002
INVENTOR(S) : Russell B. Thompson, Robert A. Kelley and Fernando Pumares It is certified that error appears in the above-identified patent and that said Letters Patent is hereby corrected as shown below:

Column 7,
Line 37, replace "shrink" with -- Shrink --

Signed and Sealed this

Second Day of November, 2004

JON W. DUDAS
*Director of the United States Patent and Trademark Office*